United States Patent [19]

Nelson et al.

[11] 4,038,299
[45] July 26, 1977

[54] 2-SUBSTITUTED-5-OXO-5H-DIBENZO [A,D] -CYCLOHEPTENE ESTERS

[75] Inventors: Peter H. Nelson; Karl G. Untch, both of Los Altos, Calif.

[73] Assignee: Syntex (U.S.A.) Inc., Palo Alto, Calif.

[21] Appl. No.: 664,779

[22] Filed: Mar. 8, 1976

Related U.S. Application Data

[60] Division of Ser. No. 581,501, May 30, 1975, Pat. No. 3,966,820, which is a continuation-in-part of Ser. No. 486,038, July 5, 1974, abandoned.

[51] Int. Cl.$^2$ .................. C07C 69/02; C07C 69/76
[52] U.S. Cl. .................. 260/410.5; 260/488 CD; 260/466; 260/476 C; 260/468 G; 260/485 L; 260/473 R; 260/474
[58] Field of Search .................. 260/590 FB, 488 CD, 260/410.5, 473 R, 476 C, 408 R, 474, 468 G, 485 L

[56] References Cited

U.S. PATENT DOCUMENTS

| 3,349,093 | 10/1967 | van der Stelt | 260/473 F |
| 3,819,693 | 6/1974 | Levine et al. | 260/473 F |
| 3,950,425 | 4/1976 | van der Burg | 260/473 F |

*Primary Examiner*—Bernard Helfin
*Assistant Examiner*—James H. Reamer
*Attorney, Agent, or Firm*—Alan M. Krubiner; William B. Walker

[57] ABSTRACT

2-Substituted-5-oxo-5H-dibenzo [a,d] cycloheptenes represented by the following formula:

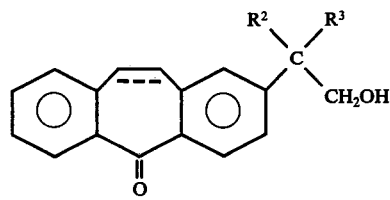

where one of $R^2$ and $R^3$ is hydrogen, and the other is hydrogen, methyl, or ethyl, or together $R^2$ and $R^3$ are methylene; the dotted line represents an optional, additional bond between the carbon atoms at the 10- and 11-positions; and the pharmaceutically acceptable esters and ethers thereof. The compounds have anti-inflammatory, analgesic, and antipyretic activities and, accordingly, are useful in the treatment of inflammation, pain and pyrexia.

25 Claims, No Drawings

2-SUBSTITUTED-5-OXO-5H-DIBENZO [A,D]-CYCLOHEPTENE ESTERS

CROSS-REFERENCE TO PARENT APPLICATION

This application is a divisional application of application Ser. No. 581,501, filed May 30, 1975 now U.S. Pat. No. 3,966,820 which, in turn, is a continuation-in-part of application Ser. No. 486,038, filed July 5, 1974, now abandoned.

FIELD OF THE INVENTION

This invention relates to novel chemical compounds. More particularly, this invention relates to novel pharmaceutically active 5-oxo-5H-dibenzo[a,d]cycloheptene derivatives substituted at the 2-position with an ethanol moiety or an α-substituted ethanol moiety, and the pharmaceutically acceptable esters and ethers thereof.

SUMMARY OF THE INVENTION

The novel 5-oxo-5H-dibenzo[a,d]cycloheptene-2-substituted derivatives of the present invention can be represented by the following formula:

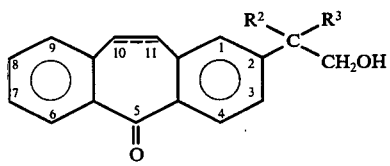

(I)

where one of $R^2$ and $R^3$ is hydrogen and the other is hydrogen, methyl, or ethyl, or together $R^2$ and $R^3$ methylene; the dotted line represents an optional, additional bond between the carbon atoms at the 10- and 11-positions; and the pharmaceutically acceptable esters and ethers thereof.

As used in this specification and claims, the term "pharmaceutically acceptable ester" denotes those hydrolyzable ester groups conventionally employed in this art, preferably those derived from hydrocarbon carboxylic acids or their salts. The term "hydrocarbon carboxylic acid" refers to both substituted and unsubstituted hydrocarbon carboxylic acids. These acids can be completely saturated or possess varying degrees of unsaturation (including aromatic), can be of straight chain, branched chain, or cyclic structure and preferably contain from 1 to 12 carbon atoms. Typical conventional hydrolyzable esters, expressed as the radical, thus included within the scope of the term as defined above are acetate, propionate, 2-methylpropionate, butyrate, valerate, caproate, enanthate, caprylate, benzoate, 2acetoxybenzoate, salicylate, phenylacetate, diethylacetate, trimethylacetate, t-butylacetate, cyclohexylacetate, cyclopentylpropionate, adamantoate, bicyclo[2.2.2]octyl carboxylate, hemisuccinate, hemiadipate, hemi-β,β-dimethylglutarate, and the like.

As used in this specification and claims, the term "pharmaceutically acceptble ether" refers to those ether groups conventionally employed in this art, preferably those derived from straight chain, branched chain, aromatic hydrocarbons and oxo heterocyclic hydrocarbons. The term "hydrocarbons" refers to both saturated and unsaturated hydrocarbons, which can be optionally substituted with groups such as hydroxy, alkoxy, halo, alkylthio, and the like. Preferably, the hydrocarbons contain from 1 to 12 carbon atoms. Typical ethers thus included within the scope of this definition include, for example, alkoxy, such as methoxy, ethoxy, propoxy, and the like; difluoromethoxy; alkoxymethoxy, such as methoxymethoxy, ethoxymethoxy, and the like; tetrahydrofuran-2'-yloxy; tetrahydropyran-2'-yloxy; and 4'-alkoxytetrahydropyran-4'-yloxy, such as 4'-methoxytetrahydropyran-4'-yloxy; and the like.

When one of $R^2$ and $R^3$ is hydrogen and the other is methyl or ethyl, the compounds of Formula I exist as pairs of enantiomorphs. Each enantiomorph or optical isomer and mixtures thereof are included within the present invention. The compounds of Formula I which exist as pairs of enantiomorphs can be administered as racemic mixtures or they can be administered as resolved enantiomorphs. In some instances, one enantiomorph exhibits greater anti-inflammatory, analgesic and/or antipyretic activity than the other corresponding enantiomorph.

The optical isomers can be resolved by conventional means, such as selective biological degradation; or by preparing the corresponding carboxylic acids, followed by preparing the diastereoisomer salts or esters thereof with an optically active amine, such as (l)-amphetamine, or an optically active alcohol such as -(d)-α-phenylethanol, separating the diastereoisomer salts or esters by fractional crystallization, cleaving the salts or esters to form the optically resolved isomer(s) of the carboxylic acid, and then converting the acid to the corresponding alcohol to thereby afford the optically resolved isomer(s) of the compound of Formula I.

Preferably, the resolved compounds of Formula I can be prepared from the corresponding resolved starting compounds used to prepare the compounds of Formula I. The resolved compounds of Formula I and the respective resolved starting compound will not necessarily have the same optical rotation, although they will have the same absolute configuration. For example, (1)-2-(5-oxo-5H-dibenzo[a,d]cyclohepten-2-yl)propan-1-ol is prepared from (d) 2-(5-oxo-5H-dibenzo[a,d]cyclohepten-2-yl)propionic acid; etc.

The compounds of Formula I exhibit anti-inflammatory, analgesic and anti-pyretic activities. Accordingly, the compositions of this invention are useful in the treatment and elimination of inflammation such as inflammatory conditions of the muscular skeletal system, skeletal joints and the other tissues, for example, the treatment of inflammatory conditions such as rheumatism, concussion, laceration, arthritis, bone fractures, post-traumatic conditions, and gout. In those cases in which the above conditions include pain and pyrexia coupled with inflammation, the instant compounds are useful for the relief of these conditions as well as the inflammation.

Administration of the active compound of Formula I in an appropriate pharmaceutical composition can be via any of the accepted modes of administration of agents for the treatment of inflammation, pain, or pyrexia. Thus, administration can be, for example, orally, parenterally, per os, or topically, in the form of solid, semi-solid or liquid dosage forms, such as, for example, tablets, suppositories, pills, capsules, powders, liquid solutions, suspensions, creams, lotions, ointments, or the like, preferably in unit dosage forms suitable for simple administration of precise dosages. The compositions of this invention will include a conventional pharmaceutical carrier or excipient and an active compound of Formula I, and, in addition, may include other medicinal agents, pharmaceutical agents, carriers, adjuvants, etc.

The preferred manner of administration is oral using a convenient daily dosage regimen which can be adjusted according to the degree of affliction. Generally, a daily dose of from 0.1 mg. to 30 mg. of the active compound of Formula I per kilogram of body weight is used. Most conditions respond to treatment comprising a dosage level of the order of 1 mg. to 10 mg. per kilogram of body weight per day. For such oral administration, a pharmaceutically acceptable non-toxic composition is formed by the incorporation of any of the normally employed excipients, such as, for example, pharmaceutical grades of mannitol, lactose, starch, magnesium stearate, sodium saccharin, talcum, cellulose, glucose, sucrose, magnesium carbonate, and the like. Such compositions take the form of solutions, suspensions, tablets, pills, capsules, powders, sustained release formulations and the like.

The active compound of Formula I may be formulated into a suppository using, for example, polyalkylene glycols, for example, polypropylene glycol, as the carrier Liquid pharmaceutically administerable compositions can, for example, be prepared by dissolving, dispersing, etc. an active compound of Formula I and optional pharmaceutical adjuvants in a carrier, such as, for example, water, saline, aqueous dextrose, glycerol, ethanol, and the like, to thereby form a solution or suspension. If desired, the pharmaceutical composition to be administered may also contain minor amounts of non-toxic auxiliary substances such as wetting or emulsifying agents, pH buffering agents and the like, such as for example, sodium acetate, sorbitan monolaurate, triethanolamine oleate, etc.

Actual methods of preparing such dosage forms are known, or will be apparent, to those skilled in this art; for example, see Remington's Pharmaceutical Sciences, Mack Publishing Company, Easton, Pennsylvania, 14th. Edition, 1970. The composition to be administered will, in any event, contain a quantity of the active compound(s) in a pharmaceutically effective amount for relief of the particular condition being treated in accordance with the teachings of this invention.

The compounds of this invention are also uterine smooth muscle relaxants and thus are useful as agents for maintaining the pregnancy of pregnant mammals, for the benefit of the mother and/or the fetus, until termination of the pregnancy is considered, from a medical point of view, to be favorable, or more favorable, for the mother and/or the fetus. It should be understood, however, that in certain instances, for example where parturition has already begun (i.e., the mother is experiencing uterine contractions, especially near full term), that administration of the compounds of this invention may not maintain the pregnant state for an indefinite period of time. Rather, in such instances, the pregnancy will, most probably, be slightly "prolonged," a factor which may be advantageous to either the mother and/or the fetus.

The compounds of this invention are also used as agents for delaying the onset of, or for postponing, parturition. As used in this application, the phrase "to delay the onset of parturition" is intended to cover that delay in parturition caused by the administration of an active compound at any time before uterine muscle contractions have begun. Thus, it is intended that the aforementioned phrase cover abortion prevention early in pregnancy (i.e., before the fetus is "viable") as well as delaying premature parturition, a term which sometimes is used with reference to that premature labor experienced later in the pregnancy when the fetus is considered to be viable. In either case, the agents are administered as prophylatic agents in that such administration tends to prevent the onset of parturition. This administration is particularly useful in the treatment of women having a history of spontaneous abortion, miscarriage or premature delivery (i.e., delivery prior to full term). Such administration is also useful where there are clinical indications that the pregnancy might be terminated prior to that time considered favorable to the mother and/or fetus.

As used in this application, the phrase "postponing parturition" is intended to cover that delay in parturition caused by the administration of an active compound after uterine muscle contractions have begun. The condition of the patient, including the time within the gestation period when the contractions have begun, the severity of the contractions and how long the contractions have taken place will affect the results achieved. For example, the effect can be to reduce the intensity and/or the duration of the contractions (the actual act of parturition being "prolonged"), or to stop the contractions altogether. In either case, the effect will be to prolong the gestation period although, depending upon the condition of the patient as described above, the effect may either be slight or, under appropriate circumstances, somewhat greater. Such administration may be to prevent spontaneous abortion, to cause the delivery to be more easily accomplished and/or less painful to the mother, or to occur at a more appropriate time and/or place.

With respect to animals, this treatment can also be utilized to synchronize the deliveries from a group of pregnant animals to happen at or about the same time, or to happen at or about a desired time and/or place, when the births can be handled with greater facility.

In all cases, administration should be consistent with best and/or accepted medical (or veterinary) practices so as to maximize the benefits to the mother and the fetus. For example, administration should not be continued so long past full term that the fetus dies in utero.

In the practice of this aspect of the present invention, an effective amount of a compound of this invention or a pharmaceutical composition containing such a compound is administered to the pregnant mammal via any of the usual and acceptable methods known in the art. The compound can be administered either singly or in combination with another compound or compounds, as defined above, or other pharmaceutical agents, carriers, adjuvants, etc. Such compound(s) or compositions can be administered orally or parenterally in the doses and in the forms (including oral, vaginal or uterine tablets or suppositories, etc.) as set forth above regarding anti-inflammatory, etc. activities. Administrations can be a single dose or up to 3 or 4 smaller doses regularly given throughout the day. The actual amount of active compound administered will, of course, depend on its relative activity for this particular utility.

The compounds of Formula I above are prepared by treating the corresponding alkanoic acid compound, for example (5-oxo-5H-dibenzo[a,d]cyclohepten-2-yl)acetic acid or 2(5-oxo-5H-dibenzo[a,d]cyclohepten-2-yl)propionic acid, or the corresponding 10,11-dihydro compounds, with lithium aluminum hydride at about 0°

C to the boiling point of the reaction medium, preferably about room temperature, for about one-fourth hour to about 4 hours, generally about 1 hour or so, in an inert organic ether, such as diethyl ether, dipropyl ether, diisopropyl ether, dibutyl ether, and the like. The ethereal solution, after addition of water, separation and filtration, is treated with manganese dioxide at about 0° C to about the boiling point of the reaction medium, also preferably about room temperature, for about 2 to about 96 hours, generally about 8 hours or so. The product compound is then isolated and purified according to standard procedures known to those skilled in this art.

The starting alkanoic acid compounds referred to above can be prepared by conducting an Arndt-Eistert reaction upon 5-oxo-5H-dibenzo[a,d]cycloheptene-2-carboxylic acid to afford (5-oxo-5H-dibenzo[a,d]cyclohepten-2-yl)-acetic acid or 2(5-oxo-5H-dibenzo[a,d]-cyclohepten-2-yl)-propionic acid. In similar manner starting with 5-oxo-10,11-dihydro-5H-dibenzo[a,d]cycloheptene-2-carboxylic acid, the corresponding 5-oxo-5H-dibenzo[a,d]cycloheptane-2-alkanoic acids can be prepared.

5-Oxo-5H-dibenzo[a,d]cycloheptene-2-carboxylic acid is prepared by esterifying 2-methylterephthalic acid with methanol, in the presence of acid catalyst, to afford the corresponding dimethyl ester which, in turn, is reacted with N-bromosuccinimide to afford 2-bromomethylterephthalic acid dimethyl ester. This diester is reacted with triphenylphosphine to afford 2,5-bis(carbomethoxy)benzyltriphenyl phosphonium bromide which is treated with benzaldehyde and a non-nucleophilic base, such as diazabicylononene, to afford, after alkaline hydrolysis, cis and trans stilbene 2,5-dicarboxylic acid. Hydrogenatin of this latter compound with hydrogen over a 5% palladium on carbon catalyst affords 2-(2-phenethyl)terephthalic acid. Treatment with polyphosphoric acid yields 5-oxo-5H-dibenzo[a,d]cycloheptane-2-carboxylic acid which can be recystallized from aqueous dimethylformamide. 5-oxo-5H-dibenzo[a,d]cycloheptene-2-carboxylic acid is prepared by successively treating 5-oxo-5H-dibenzo[a,d]cycloheptane-2-carboxylic acid with diazomethane, N-bromosuccinimide, and dimethylformamide/diazabicyclononene, followed by base hydrolysis and acidification.

In the Arndt-Eistert reaction, the carboxylic chain of the starting 2-carboxylic acid compound is elongated by treating the 2-carboxy compound with thionyl chloride to obtain the acid chloride. This acid chloride is reacted with the diazomethane to form a diazoketone which is rearragned by the action of a silver salt in the presence of an alcohol, for example, methanol or ethanol. The resultant alkyl ester of the 2-acetic acid compound can be hydrolyzed to afford the free 2-acetic acid. Or, the resultant compound can be treated with an alkali metal hydride, amide, or dialkyl amide, such as sodium hydride, lithium isopropylcyclohexyl amide or sodium dimethyl amide, followed by treatment with an alkyl halide, such as methyl iodide or ethyl iodide, to α-alkylate the 2-acetic acid ester compound, thereby forming the corresponding 2-propionic acid ester or the 2-butyric acid ester, which also can be hydrolyzed to form the corresponding 2-propionic acid or 2-butyric acid compounds, respectively. Optionally, the 2-propionic acid compound can be prepared, without the need for α-methylation, by reacting 2-chloroformyl-5-oxo-5H-dibenzo[a,d]cycloheptene with ethereal diazoethane, followed by treatment with N,N-dimethylaniline and benzyl alcohol, base hydrolysis and acidification. The Arndt-Eistert reaction is a well-known series of steps, the particulars of which can be determined by reference to the Examples below or to the articles thereon in the published literature.

The α,α-methylene group is introduced by treating the 2-carboxy compound with thionyl chloride, then ethereal diazomethane to afford the corresponding 2-diazoacetyl compound, which is then treated with aqueous acid and copper powder in a water-miscible, organic solvent at elevated temperatures to afford the corresponding 2-hydroxyacetal compound. The latter compound is reacted, at elevated temperatures, with methylene iodide in the presence of a zinc-copper couple to afford the corresponding α,α-methylene-ethan-1-ol compound.

The compounds of Formula I can be esterified or etherified via conventional techniques. For example, the compounds can be esterified by treatment with an acid anhydride, such as acetic anhydride, valeric anhydride, caproic anhydride, and the like, in pyridine; or by treatment with an acid chloride, such as acetyl chloride, adamantoyl chloride, and the like, in acetonitrile and triethylamine; or by treatment with a carboxylic acid in the presence of an acid catalyst, such as p-toluenesulfonic acid, and the like. The compounds of Formula I can be etherified by treatment with an alkali metal hydride, such as sodium hydride, and an organic halide, such as cyclopentyl chloride, 2-chlorotetrahydropyran, 2-chlorotetrahydrofuran, and the like; or by treatment with dihydrofuran, dihydropyran, 4-methoxydihydropyran, and the like, in the presence of an acid catalyst.

In each of the process steps, described herein above and below, unless otherwise indicated, the respective intermediate products are preferably separated from the reaction mixture and purified prior to their use as starting materials for the next step in the process. Such separation and purification can be effected by any suitable procedure For example, typical separation procedures include filtration, extract ion, evaporation, and typical purification procedures include crystallization, and both thin-layer and column chromatography. Optimum separation and isolation procedures can be obtained for any given step by routine experimentation as will be apparent to those skilled in this art.

Particular compounds falling within the scope of the present invention can be prepared by selecting an appropriate starting material, for example, from those referred to above, and then selecting particular reaction step or steps, as for example described above, to give the compound desired. In view of this disclosure, the preparation of particular compounds, including compounds falling within the present invention but not specifically described in this specification, will be apparent to those skilled in this art.

In this specification, the 2-substituted-10,11-dihydro-5-oxo-5H-dibenzo[a,d]cycloheptenes of this invention are also referred to as the corresponding 2-substituted-5-oxo-5H-dibenzo[a,d]cycloheptanes, it being understood that both designations refer to the compounds of Formula I where there is a single bond between the carbon atoms at the 10- and 11-positions.

Exemplary of the compounds of the present invention, as represented by the structural formula above, are the following illustrated compounds:

2-(5-oxo-5H-dibenzo[a,d]cyclohepten-2-yl)ethan-1-ol;

2-(5-oxo-5H-dibenzo[a,d]cycloheptan-2-yl)propan-1-ol;
2-(5-oxo-5H-dibenzo[a,d]cyclohepten-2-yl)butan-1-ol;
2-(5-oxo-5H-dibenzo[a,d]cyclohepten-2-yl)prop-1-en-3-ol;
2-(5-oxo-5H-dibenzo[a,d]cyclohepten-2-yl)eth-1-yl acetate;
2-(5-oxo-5H-dibenzo[a,d]cyclohepten-2-yl)prop-1-yl acetate;
2-(5-oxo-5H-dibenzo[a,d]cyclohepten-2-yl)but-1yl acetate;
2-(5-oxo-5H-dibenzo[a,d]cyclohepten-2-yl)prop-1-en-3-yl acetate;
2-(5-oxo-5H-dibenzo[a,d]cyclohepten-2-yl)eth-1-yl propionate;
2-(5-oxo-5H-dibenzo[a,d]cyclohepten-2-yl)prop-1-yl propionate;
2-(5-oxo-5H-dibenzo[a,d]cyclohepten-2-yl)but-1-yl propionate;
2-(5-oxo-5H-dibenzo[a,d]cyclohepten-2-yl)prop-1en-3-yl propionate;
2-(5-oxo-5H-dibenzo[a,d]cyclohepten-2-yl)prop-1-yl n-butyrate;
2-(5-oxo-5H-dibenzo[a,d]cyclohepten-2-yl)prop-1-yl 3'-methylbutyrate;
2-(5-oxo-5H-dibenzo[a,d]cyclohepten-2yl)prop-1-yl n-pentanoate;
2-(5-oxo-5H-dibenzo[a,d]cyclohepten-2-yl)prop-1-yl n-hexanoate;
2-(5-oxo-5H-dibenzo[a,d]cycloheptan-2-yl)ethan-1-ol;
2-(5-oxo-5H-dibenzo[a,d]cycloheptan-2-yl)propan-1-ol;
2-(5-oxo-5H-dibenzo[a,d]cycloheptan-2-yl)butan-1-ol;
2-(5-oxo-5H-dibenzo[a,d]cycloheptan-2-yl)prop-1en-3-ol;
2-(5-oxo-5H-dibenzo[a,d]cycloheptan-2-yl)eth-1-yl acetate;
2-(5-oxo-5H-dibenzo[a,d]cycloheptan-2yl)prop-1-yl acetate;
2-(5-oxo-5H-dibenzo[a,d]cycloheptan-2-yl)but-1-yl acetate;
2-(5-oxo-5H-dibenzo[a,d]cycloheptan-2-yl)prop-1en-3-yl acetate;
2-(5-oxo-5H-dibenzo[a,d]cycloheptan-2yl)eth-1-yl propionate;
2-(5-oxo-5H-dibenzo[a,d]cycloheptan-2-yl)prop-1-yl propionate;
2-(5-oxo-5H-dibenzo[a,d]cycloheptan-2-yl)but-1-yl propionate;
2-(5-oxo-5H-dibenzo[a,d]cycloheptan-2-yl)prop-1en-3-yl proprionate;
2-(5-oxo-5H-dibenzo[a,d]cycloheptan-2-yl)prop-1-yl butyrate;
2-(5-oxo-5H-dibenzo[a,d]cycloheptan-2-yl)prop-1-yl 3'-methylbutyrate;
2-(5-oxo-5H-dibenzo[a,d]cycloheptan-2-yl)prop-1-yl n-pentanoate;
2-(5-oxo-5H-dibenzo[a,d]cycloheptan-2-yl)prop-1-yl n-hexanoate;
1-ethoxy(or 2-tetrahydropropanyl ether)-2-(5-oxo-5H-dibenzo[a,d]cyclohepten-2-yl)propane;
and the corresponding *l* and *d* isomers of those compounds which have an assymetric carbon atom.

DESCRIPTION OF SPECIFIC EMBODIMENTS

The following specific description is given to enable those skilled in this art to more clearly understand and practice the present invention. It should not be considered as a limitation upon the scope of the invention but merely as being illustrative and representative thereof.

Preparation 1

148 G. of 2-methylterephthalic acid is refluxed for 24 hrs. in 750 ml. of dry methanol containing 30 ml. of sulphuric acid. The solution is cooled, poured into water and extracted with ether. The extract is washed, dried and evaporated to give dimethyl-2-methylterephthalate.

88 G. of dimethyl-2-methylterephthalate in 1000 ml. of carbon tetrachloride containing 89 g. (1 mole) of N-bromosuccinimide is refluxed for 3 hours using a heat lamp. The solution is cooled, filtered and evaporated to dryness to give dimethyl -2-bromomethylterephthalate 25.7 G. of dimethyl-2-bromomethylterephthalate is refluxed in 250 ml. of acetonitrile containing 26.2 g. (1 mole) of triphenylphosphine for 4 hrs. The solution is cooled and diluted with 1250 ml. of ether thereby precipitating 2,5-bis(carbomethoxy)-benzyltriphenylphopshonium bromide which is filtered off and dried under vacuum.

51.9 G. of 2,5-bis(carbomethoxy)-benzyltriphenylphosphonium bromide and 10.6 g. of benzaldehyde are stirred in 300 ml. of acetonitrile and 12.4 g. of diazabicyclononene is added. The mixture is heated briefly to reflux, then cooled and evaporated to an oil. The oil is dissolved in ethyl acetate, and the solution washed with dilute hydrochloric acid, dried and evaporated. The residue is refluxed for 12 hrs. in a solution of 20 g. of potassium hydroxide in 300 ml. of water and 50 ml. of methanol. The solution is cooled and extracted with chloroform. The aqueous solution is acidified with dilute hydrochloric acid and the precipitated cis and trans stilbene-2,5-dicarboxylic acid is filtered off and dried.

23.6 G. of cis and trans-stilbene-2,5-dicarboxylic acid is dissolved in 100 ml. of dimethylformamide containing 500 mg. of 5% palladium on carbon and hydrogenated for 2 hrs. The solution is filtered and evaporated to dryness to give a crude product which upon recrystallization from aqueous ethanol yields 2-(2-phenethyl)-terephthalic acid.

23.8 G. of 2-(2-phenethyl)terephthalic acid is dissolved in 200 ml. of sulpholane at 130° C and 150 ml. of polyphosphonic acid is added with stirring. The mixture is stirred at 130° C for 4 hrs., then poured into 1000 ml. of water. The product is filtered off and recrystallization from aqueous dimethylformamide to yield 5-oxo-5H-dibenzo[a,d]cycloheptane-2-carboxylic acid.

Preparation 2

5.0 G. of 5-oxo-5H-dibenzo[a,d]cycloheptane-2-carboxylic acid (as prepared in Preparation 1 above) is suspended in 50 ml. of dioxane, added to excess ethereal diazomethane, and stirred until dissolution is complete. The solution is then evaporated to dryness to yield 2-carbomethoxy-5-oxo-5H-dibenzo[a,d]cycloheptane.

4.68 G. of 2-carbomethoxy-5-oxo-5H-dibenzo[a,d]cycloheptane is refluxed in 100 ml. of carbon tetrachloride containing 3.56 g. (1 eg.) of N-bromosuccinimide while being irradiated with a 100 watt incandescent lamp. After 2 hrs. the solution is cooled, filtered and evaporated to dryness. The residue is dissolved in 30 ml. of dimethylformamide and 2.48 g. (1 eg.) of diazabicyclononene is added. The mixture is heated briefly to 60° C, and water and ethyl acetate are added. The organic layer is washed with dilute hydrochloric acid and water, then dried and evaporated to give 2-carbomethoxy-5-oxo-5H-dibenzo[a,d]cycloheptene. Hydrolysis in eight to one aqueous methanol, 5% potassium hydroxide, followed by acidification with dilute hydrochoric acid yields 5-oxo-5H-dibenzo[a,d]cycloheptene-2-carboxylic acid.

Preparation 3

22 G. of 5-oxo-5H-dibenzo[a,d]cycloheptane-2-carboxylic acid is stirred in 200 ml. of chloroform, 50 ml. of thionyl chloride and 1 ml. of dimethylformamide for 8 hrs. The mixture is evaporated to dryness and the residue recrystallized from acetonitrile to yield 2-chloroformyl-5-oxo-5H-dibenzo[a,d]cycloheptane. This is dissolved in 200 ml. of chloroform and added to a 3-fold excess of ethereal diazomethane at 0° C. The mixture is left at 0° C for 12 hrs. then evaporated to dryness. The residue is recrystallized from acetonitrile to yield 2-diazoacetyl-5-oxo-5H-dibenzo[a,d]cycloheptane. The diazoketone is heated to reflux in 250 ml. of ethanol and a saturated triethylamine solution of 2 g. of silver benzoate is added slowly until gas evolution ceases. The solution is cooled, filtered and evaporated to yield ethyl (5-oxo-5H-dibenzo[a,d]cycloheptan-2-yl)acetate. This ester is refluxed in 5% aqueous potassium hydroxide for 12 hrs. The solution is cooled, acidified with dilute hydrochloric acid and extracted with ether. The ether extract is dried and evaporated to yield (5-oxo-5H-dibenzo[a,d]cycloheptan-2-yl)acetic acid which can be recrystallized from acetone-hexane.

Preparation 4

Lithium isopropylcyclohexylamide is prepared by adding 10 mls. of 1.0 molar n-butyl lithium to a solution of 1.41 g. of isopropylcyclohexylamine in 100 ml. of dry tetrahydrofuran. To this solution, cooled to −80° C, there is added a solution of 2.82 g. of ethyl (5-oxo-5H-dibenzo[a,d]cycloheptan-2-yl)acetate (as prepared in Preparation 3 above) in 10 ml. of tetrahydrofuran. The mixture is left for 5 minutes, then 1.42 g. of methyl iodide is added. The reaction is allowed to attain room temperature, then water and ether are added. The ethereal layer is washed with dilute hydrochoric acid and water, dried and evaporated to yield ethyl 2-(5-oxo-5H-dibenzo[a,d]cycloheptan-2-yl)propionate. This ethyl ester is refluxed for 12 hrs. in 5% aqueous potassium hydroxide, followed by acidification with dilute hydrochloric acid and ether extraction to afford 2-(5-oxo-5H-dibenzo[a,d]cycloheptan-2-yl)propionic acid.

In a similar manner substituting ethyl iodide for the methyl iodide above, there is prepared 2-(5-oxo-5H-dibenzo[a,d]cycloheptan-2-yl)butyric acid.

Preparation 5

In similar manner to the procedure of Preparations 3 and 4 substituting 5-oxo-5H-dibenzo[a,d]cycloheptene-2-carboxylic acid for the 5-oxo-5H-dibenzo[a,d]cycloheptane-2-carboxylic acid of Preparation 3, there is prepared ethyl (5-oxo-5H-dibenzo[a,d]cyclohepten-2-yl)acetate, (5-oxo-5H-dibenzo[a,d]cyclohepten-2-yl)acetic acid, 2-(5-oxo-5H-dibenzo[a,d]cyclohepten-2-yl)propionic acid, and 2-(5-oxo-5H-dibenzo[a,d]cyclohepten-2-yl) acid.

EXAMPLE I 0.5 G. of lithium aluminum hydride is added to a solution of 2.78 g. of 2-(5-oxo-5H-dibenzo[a,d]cyclohepten-2-yl)propionic acid in 200 ml. of anhydrous ether. The mixture is stirred for 2 hours and then excess hydride is destroyed by sequential addition of ethyl acetate, methanol and water. The ethereal solution is separated and filtered and to it is added 15 g. of activated manganese dioxide. The mixture is stirred for 8 hours, then filtered through 10 g. of silica gel and the eluate evaporated to afford 2-(5-oxo-5H-dibenzo[a,d]cyclohepten-2-yl)propan-1-ol (m.p. 63°66° C).

In similar manner substituting:
(5-oxo-5H-dibenzo[a,d]cyclohepten-2-yl)acetic acid,
2-(5-oxo-5H-dibenzo[a,d]cyclohepten-2-yl)butyric acid,
(5-oxo-5H-dibenzo[a,d]cycloheptan-2-yl)acetic acid,
2-(5-oxo-5H-dibenzo[a,d]cycloheptan-2-yl)propionic acid, or
2-(5-oxo-5H-dibenzo[a,d]cycloheptan-2-yl)butyric acid, for the 2-(5-oxo-5H-dibenzo[a,d]cyclohepten-2-yl)propionic acid, the following are prepared:
2-(5-oxo-5H-dibenzo[a,d]cyclohepten-2-yl)ethan-1-ol,
2-(5-oxo-5H-dibenzo[a,d]cyclohepten-2-yl)butan-1-ol,
2-(5-oxo-5H-dibenzo[a,d]cycloheptan-2-yl)ethan-1-ol,
2-(5-oxo-5H-dibenzo[a,d]cycloheptan-2-yl)propan-1-ol,
[a gum; nmr spectrum in deuterochloroform relative to tetramethylsilane: 1.25 (doublet, $CH_3$), 1.60 (singlet, OH), 3.16 (singlet, 10H, 11H) and 3.70 ppm (doublet, $CH_2OH$)], and
2-(5-oxo-5H-dibenzo[a,d]cycloheptan-2-yl)butan-1-ol, respectively.

EXAMPLE II

A solution of 2.50 g. of 2-carboxy-5-oxo-5H-dibenzo[a,d]cycloheptene in 50 ml. of chloroform, 10 ml. of thionyl chloride and 0.3 ml. of dimethylformamide is stirred for 8 hours, then evaporated to dryness and the residue recrystallized from acetonitrile to yield 2-chloroformyl-5-oxo-5H-dibenzo[a,d]cycloheptene.

This is dissolved in 50 ml. of chloroform and added to a 3-fold excess of ethereal diazomethane at 0° C. After 12 hours the solution is evaporated to dryness and the residue recrystallized from acetonitrile to yield 2-diazoacetyl-5-oxo-5H-dibenzo[a,d]cycloheptene. A solution of 1.37 g. of the latter compound in 50 ml. of tetrahydrofuran is added to 10 ml. of 0.1 N sulfuric acid containing 0.5 g. of copper powder. The mixture is refluxed for 3 hours and then cooled, filtered and poured into water. The solution is extracted with ethyl acetate and the extract washed, dried and evaporated to yield 2-hydroxyacetyl-5-oxo-5H-dibenzo[a,d]cycloheptene which is recrystallized from chloroform/hexane. A solution of 0.05 g. of cupric acetate monohydrate in 5 ml. of acetic acid is heated to 100° C and 3.0 g. of granular zinc is added. The mixture is shaken for 3 minutes and the acetic acid is then decanted. The residual zinc-copper couple is washed three times with 5 ml. portions of acetic acid, then three times with 5 ml. portions of ether. It is then refluxed for 4 hours under nitrogen in 20 ml. of ether containing 2.5 ml. of methylene iodide, 1.32 g. of 2-hydroxyacetyl-5-oxo-5H-dibenzo[a,d]cycloheptene is added, and reflux is continued for a further 4 hours. The mixture is cooled and diluted with 50 ml. of benzene. The liquid phase is decanted and washed with water and aqueous sodium bisulfate, then dried and evaporated. The residue is chromatographed on 50 gm. of silica gel, eluting with ethyl acetate/hexane, to yield 2-(5-oxo-5H-dibenzo[a,d]cyclohepten-2-yl)prop-1-en-3-ol.

In similar manner substituting 2-carboxy-5-oxo-5H-dibenzo[a,d]cycloheptane for the 2-carboxy-5-oxo-5H-dibenzo[a,d]cycloheptene, there is prepared 2-(5-oxo-5H-dibenzo[a,d]cycloheptan-2-yl)prop-1-en-3-ol.

EXAMPLE III 0.5 G. of 2-(5-oxo-5H-dibenzo[a,d]cyclohepten-2-yl)propan-1-ol is dissolved in 15 ml. of acetonitrile and 2 ml. of acetyl chloride and 1.3 ml. of triethylamine are added to the solution. After 1 hour, the mixture is poured into water and extracted with ethyl acetate. The extract is dried and evaporated, then dissolved in ether and passed through a silica gel column, and the eluate evaporated to afford 2-(5-oxo-5H-dibenzo[a,d]cyclohepten-2-yl)prop-1-yl acetate [an oil, nmr spectrum in deuterochloroform relative to tetramethylsilane, 1.33 (doublet, $CH_3$), 1.98 (singlet, acetoxy), 4.23 (doublet, $CH_2$) and 7.02 ppm (singlet, 10H, 11H); mass spectrum: 306 (M+), 246, 234].

In a similar manner, substituting any of the other alcohols prepared in Examples I and II above for the 2-(5-oxo-5H-dibenzo[a,d]cyclohepten-2-yl)propan-1-ol the corresponding acetates are prepared.

Also in similar manner using any of the alcohols prepared in Examples I and II above and substituting propionyl chloride, butyryl chloride, valeryl chloride, isovaleryl chloride, caproyl chloride, capryl chloride, benzoyl chloride, phenylacetyl chloride, diethylacetyl chloride, trimethylacetyl chloride, and cyclopentylpropionyl chloride for the acetyl chloride, the corresponding esters are prepared, including 2-(5-oxo-5H-dibenzo[a,d]cyclohepten-2-yl)prop-1-yl 3'-methylbutyrate (m.p. 79°–80° C) and 2-(5-oxo-5H-dibenzo[a,d]cyclohepten-2-yl)prop-1-yl dodecanoate (m.p. 40°–41° C).

EXAMPLE IV 0.45 G. of 2-(5-oxo-5H-dibenzo[a,d]cyclohepten-2-yl)propan-1-ol is dissolved in 6 ml. of ether, and to the solution is added 0.216 g. of dihydropyran and 0.001 g. of p-toluenesulphonic acid. After 24 hours, a few drops of triethylamine are added. The solution is then poured into water and extracted with ethyl acetate. The extract is dried and evaporated and the residue chromatographed on silica gel, eluting with hexane:ethyl acetate (5:1), to afford 2-(5-oxo-5H-dibenzo[a,d]cyclohepten-2-yl)prop-1-yl 2'-tetrahydropyranyl ether [an oil; nmr spectrum in deuterochloroform relative to tetramethylsilane: 1.44 (doublet, $CH_3$), 4.55 (multiplet, O—CH—O) and 7.00 ppm (singlet, 10H, 11H); mass spectrum: 348 (M+) 248, 234].

In similar manner, substituting dihydrofuran, and 4-methoxydihydropyran for the dihydropyran, 2-(5-oxo-5H-dibenzo[a,d]cyclohepten-2-yl)prop-1-yl tetrahydrofuran-2-yl ether and 2-(5-oxo-5H-dibenzo[a,d]cyclohepten-2-yl)prop-1-yl 4'-methoxytetrahydropyran-4'-yl ether are prepared.

Also in similar manner substituting any of the alcohols prepared in Examples I and II above for the 2-(5-oxo-5H-dibenzo[a,d]cyclohepten-2-yl)propan-1-ol, the corresponding ethers are prepared.

EXAMPLE V 0.48 G. of a 50% mineral oil dispersion of sodium hydride is added to a solution of 2.64 g. of 2-(5-oxo-5H-dibenzo[a,d]cyclohepten-2-yl)propan-1-ol in 30 ml. of dimethylformamide. The mixture is warmed to 40° C and stirred until hydrogen evolution ceases. 3.0 G. of ethyl iodide is added and the mixture heated to 60° C for 3 hrs. Water and ether are added and the ethereal solution is washed with water, dried and evaporated to yield 1-ethoxy-2-(5-oxo-5H-dibenzo[a,d]cyclohepten-2-yl)propane.

In similar manner, substituting methyl iodide, propyl iodide, 2-butyl iodide, 3-methylbutyl iodide, chloromethyl methyl ether or chloromethyl ethyl ether for the ethyl iodide, the corresponding ethers are prepared. Also in similar manner, using any of the alcohols prepared above, the corresponding ethers are prepared.

EXAMPLE VI

1 G. of 2-acetoxybenzoic acid is added to a solution of 2 ml. of trifluoroacetic anhydride in 10 ml. of benzene. After 1 hour, the solution is evaporated and to the residue is added 10 ml. of benzene followed by the addition of 1 g. of 2-(5-oxo-5H-dibenzo[a,d]cyclohepten-2-yl)propan-1-ol. After 1 hour at room temperature, the mixture is added to sodium bicarbonate solution. The benzene layer is separated, washed with water and evaporated to dryness to afford, upon recrystallization, 2-(5-oxo-5H-dibenzo[a,d]cyclohepten-2-yl)prop-1-yl 2'-acetoxybenzoate.

In a similar manner using 2-(5-oxo-5H-dibenzo[a,d]cycloheptan-2-yl)propan-1-ol, there is prepared 2-(5-oxo-5H-dibenzo[a,d]cycloheptan-2-yl)prop-1-yl 2'-acetoxybenzoate.

Also in similar manner, substituting salicylic acid for the 2-acetoxybenzoic acid, the corresponding salicylate esters are prepared.

In similar manner, substituting any of the alcohols prepared above for the 2-(5-oxo-5H-dibenzo[a,d]cyclohepten-2-yl)propan-1-ol, the corresponding esters are prepared.

EXAMPLE VII 2.78 G. of 2-(5-oxo-5H-dibenzo[a,d]cyclohepten-2-yl)propionic acid is stirred in a mixture of 20 ml. of benzene and 5 ml. of trifluoroacetic anhydride for 15 minutes. The mixture is evaporated to dryness and redissolved in 20 ml. of dry benzene. A mixture of 1.0 g. of pyridine and 2.44 g. (2 egs.) of (+) α-phenylethanol is added. The mixture is left for 30 minutes and then water and ether are added. The organic layer is washed with dilute hydrochloric acid and water, then dried and evaporated. The residue is chromatographed on 100 gm. silica gel, eluting with hexane:ether (4:1) to afford a 1:1 mixture of diastereomeric esters. Repeated crystallization of this mixture from ether-hexane yields the less soluble isomer. The purity of samples from successive recrystallizations is monitored by gas-liquid chromotography using a 1 meter × 2 mm. column packed with Chromosorb W (Regis Chemical Co., Chicago, Ill.) impregnated with 3% w/w OV101 polymeric material (Applied Sciences Laboratory, Inc., State College, Penn.) as stationry phase, and helium as the carrier gas at 220° C. The less soluble isomer is decomposed by stirring in a mixture of 5 ml. of benzene and 5 ml. of trifluoroacetic acid for 30 minutes. Water and ether are added and the ethereal layer washed with water, and then with dilute aqueous sodium carbonate. The aqueous layer is acidified with dilute hydrochloric acid and then extracted with ether. The ethereal layer is washed, dried and evaporated to give the resolved (d)-2-(5-oxo-5H-dibenzo[a,d]cyclohepten-2-yl)propionic acid which is recrystallized from acetone-hexane. The 1-isomer can be obtained in similar manner using (−) α-phenylethanol.

2.8 G. (0.01) mole of 2-(5-oxo-5H-dibenzo[a,d]cycloheptan-2-yl)propionic acid is dissolved in 25 ml. of isopropanol and 1.35 g. (0.01 mole) of l-amphetamine is added. The salt crystallizes out and is filtered off and recrystallized several times from isopropanol to constant specific rotation. The salt is suspended in ether and dilute hydrochloride is added. After shaking, the organic layer is washed, dried and evaporated to give the resolved (d)-2-(5-oxo-5H-dibenzo[a,d]cycloheptan-2-yl)propionic acid which can be recrystallized from acetone-hexane. The 1-isomer can be obtained in similar manner using d-amphetamine.

In a similar manner to the procedure of Example I above, substituting (d)-2-5-oxo-5H-dibenzo[a,d]cyclohepten-2-yl)propionic acid, (1)-2-(5-oxo-5H-dibenzo[a,d]cyclohepten-2-yl)propionic acid, (d)-2-(5-oxo-5H-dibenzo[a,d]cycloheptan-2-yl)propionic acid, or (1)-2-(5-oxo-5H-dibenzo[a,d]cycloheptan-2-yl)propionic acid for 2-(5-oxo-5H-dibenzo[a,d]cyclohepten-2-yl)propionic acid, (1)-2-(5-oxo-5H-dibenzo[a,d]cyclohepten-2-yl)propan-1-ol, (d)-2-(5-oxo-5H-dibenzo[-a,d]cyclohepten-2-yl)propan-1-ol [an oil; $[\alpha]_D + 19.0°$ (in chloroform, 5 mg./ml.)], (1)-2-(5-oxo-5H-dibenzo[-a,d]cyclohepten-2-yl)propan-1-ol, (d)-2-(5-oxo-5H-dibenzo[a,d]cycloheptan-2-yl)propan-1-ol [an oil; $[\alpha]_D + 14.4°$ (in chloroform, 5 mg./ml.)] are prepared, respectively.

EXAMPLE VIII 0.45 G. of methyl(5-oxo-5H-dibenzo[a,d]cyclohepten-2-yl)acetate is dissolved in 10 ml. of ether/tetrahydrofuran (1:1) and excess lithium aluminum hydride is added. After 3 hours, excess hydride is destroyed by addition of water and the mixture is extracted with ether. The extract is dried and to it is added 2.0 g. of manganese dioxide. The mixture is left for 4 days and then filtered through celite and evaporated. The residue is recrystallized from hexane to afford 2-(5-oxo-5H-dibenzo[a,d]-cyclohepten-2-yl)ethan-1-ol (m.p. 73°–75° C).

EXAMPLE IX

The anti-inflammatory activity of the following compounds embraced within this invention were compared with the activity of phenylbutazone by means of the carrageenin-induced rat paw inflammation test described below.

TEST FOR ANTI-INFLAMMATORY ACTIVITY UTILIZING CARRAGEENIN INDUCED PAW INFLAMMATION IN THE RAT

Materials and Methods — Female rats weighing 80–90 grams are used. The test materials are given at hour 0 orally by gavage in 1 ml. aqueous vehicle. At hour 1, 0.05 ml. of a 1% solution (in 0.9% NaCl) of carrageenin is injected into the right hind paw. This injection causes an inflammation of the paw. The rats are sacrificed at hour 4, at which time both hind paws are removed and weighed separately.

End point: % increase in paw size calculated as follows:

$$\frac{\text{Wt. of Right Paw} - \text{Wt. of Left Paw}}{\text{Wt. of Left Paw}} \times 100$$

The results of these tests are summarized in the following table:

| Compound | Oral Anti-Inflammatory Activity (Phenylbutazone = 1) |
| --- | --- |
| 2-(5-oxo5H-dibenzo-[a,d]cyclohepten-2-yl)-ethan-1-ol | 5 |
| 2-(5-oxo-5H-dibenzo[a,d]cyclohepten-2-yl-propan-1-ol | 6 |
| 2-(5-oxo-5H-dibenzo-[a,d]cyclohepten-2-yl)-prop-1-yl acetate | ≧3 |
| 2-(5-oxo-5H-dibenzo-[a,d]cyclohepten-2-yl)-prop-1-yl 3'-methyl-butyrate | 8 |
| 2-(5-oxo-5H-dibenzo-[a,d]cyclohepten-2-yl)-prop-1-yl dodecanoate | 6 |
| 2-(5-oxo-5H-dibenzo-[a,d]cyclohepten-2-yl)-prop-1-yl 2'-tetrahydro-pyranyl ether | 6 |

2-(5-Oxo-5H-dibenzo[a,d]cyclohepten-2-yl)propan-1-ol was also tested for analgesic activity in the well-known mouse analgesic (anti-writhing) assay and was found to be at least equipotent, in this assay, with aspirin.

EXAMPLE X

A suspension is prepared having 200 mg. of 2-(5-oxo-5H-dibenzo[a,d]cyclohepten-2-yl)propan-1-ol, 0.1% Tween 80 (sorbitan monoleate polyoxyethylene; a product of Atlas Chemical Inudstries, Inc.) and 0.5% sodium carboxymethyl cellulose per ml. of simple syrup (U.S.P.).

EXAMPLE XI

A solution is prepared having 100 mg. of 2-(5-oxo-5H-dibenzo[a,d]cyclohepten-2-yl)propan-1-ol per ml. of solution of 70% ethanol and 30% simple syrup (U.S.P.).

EXAMPLE XII

| Ingredients | Quantity per tablet, mgs. |
| --- | --- |
| 2-(5-oxo-5H-dibenzo[a,d]-cyclohepten-2-yl)-propan-1-ol | 300 |
| cornstarch (paste) | 30 |
| magnesium stearate | 0.5 |
| lactose | 100 |

The above ingredients are thoroughly mixed and pressed into single scored tablets.

EXAMPLE XIII

| Ingredients | Quantity per tablet, mgs. |
| --- | --- |
| 2-(5-oxo-5H-dibenzo[a,d]-cyclohepten-2-yl)propan-1-ol | 250 |
| cornstarch | 30 |
| magnesium stearate | 0.5 |
| polyvinylpyrrolidone | 25 |
| lactose | to 400 |

The above ingredients are thoroughly mixed and pressed into single scored tablets.

EXAMPLE XIV

| Ingredients | Quantity per capsule, mgs. |
| --- | --- |
| 2-(5-oxo-5H-dibenzo[a,d]-cyclohepten-2-yl)propan-1-ol | 250 |
| cornstarch | 25 |
| lactose | to 350 |

The above ingredients are mixed and introduced to a hard-shell gelatin capsule.

EXAMPLE XV

| Ingredients | Quantity per capsule, mgs. |
| --- | --- |
| 2-(5-oxo-5H-dibenzo-[a,d]cyclohepten-2-yl)-propan-1-ol | 300 |
| lactose | 150 |
| magnesium stearate | 8 |

The above ingredients are mixed and introduced to a hard-shell gelatin capsule.

EXAMPLE XVI

A suppository totaling 2.8 grams is prepared having the following composition:

| | |
| --- | --- |
| 2-(5-oxo-5H-dibenzo[a,d]cyclo-hepten-2-yl)propan-1-ol | 150 mg. |
| Witepsol H-15 (triglycerides of saturated vegetable fatty acids; a product of Riches-Nelson, Inc., New York, N.Y.) | balance |

EXAMPLE XVII

To a solution of 0.25 g. of 2-(5-oxo-5H-dibenzo[a,d]-cyclohepten-2-yl)propionyl chloride in 20 ml. of acetonitrile is added 0.20 g. of 2-(5-oxo-5H-dibenzo[a,d]cyclohepten-2-yl)propan-propan-1-ol and 0.40 ml. of triethylamine. The mixture is left for 16 hours, then evaporated to dryness. The residue is dissolved in ethyl acetate and the solution is washed with water, dilute hydrochloric acid and aqueous sodium carbonate, then dried and evaporated. The product is chromatographed on silica gel, eluting with benzene, to afford 2'-(5-oxo-5H-dibenzo[a,d]cyclohepten-2-yl)prop-1'-yl 2-(5-oxo-5H-dibenzo[a,d]cyclohepten-2-yl)propionate [a gum; nmr spectrum in deuterochloroform relative to tetramethylsilane: 1.23 (doublet, CH$_3$), 1.46 (doublet, CH$_3$), ca. 4.2 (multiplet, CH$_2$O) and ca. 6.8 p.p.m. (multiplet, 10H, 11H); Mass spectrum: 524 (m+) 278, 246, 205].

The propionyl chloride starting material is prepared by dissolving 1.0 g. of 2-(5-oxo-5H-dibenzo[a,d]cyclohepten-2-yl)propionic acid in 25 ml. of chloroform. 1 M1. of thionyl chloride and 0.1 ml. of dimethylformamide are added thereto and the mixture left for 1 hour, then evaporated to dryness under vacuum to yield the desired product.

In similar manner, substituting 2-(5-oxo-5H-dibenzo[-a,d]-cycloheptan-2-yl)propan-1-ol for the 2-(5-oxo-5H-dibenzo[a,d]-cyclohepten-2-yl)propan-1-ol, there is obtained 2'-(5-oxo-5H-dibenzo[a,d]cycloheptan-2-yl)prop-1'-yl 2-(5-oxo-5H-dibenzo[a,d]cyclohepten-2-yl)propionate. Also in similar manner, using the appropriate starting materials, 2'-(5-oxo-5H-dibenzo[a,d]cyclohepten-2-yl)prop-1'-yl 2-(5-oxo-5H-dibenzo[a,d]cycloheptan-2-yl)propionate and 2'-(5-oxo-5H-dibenzo[a,d]cycloheptan-2-yl)prop-1'-yl 2-(5-oxo-5H-dibenzo[a,d]cycloheptan-2-yl)propionate are prepared.

Also in similar manner using the corresponding optical isomers of the above alcohols and acids, the respective esters are prepared, including, for example, (1) 2'-(5-oxo-5H-dibenzo[a,d]cyclohepten-2-yl)prop-1'-yl (d) 2-(5-oxo-5H-dibenzo[a,d]-cyclohepten-2-yl)propionate.

Separation or purification of the desired product (s) can be by conventional techniques, for example from those described hereinabove.

While the present invention has been described with reference to specific embodiments thereof, it should be understood by those skilled in this art that various changes may be made and equivalents may be substituted without departing from the true spirit and scope of the invention. In addition, many modifications can be made to adapt a particular situation, material or composition of matter, process, process step or steps, or then-present objective to the spirit of this invention without departing from its essential teachings.

What is claimed is:

1. The pharmaceutically acceptable esters of a hydrocarbon carboxylic acid of from 1 to 12 carbon atoms and a compound selected from the group of compounds represented by the formula:

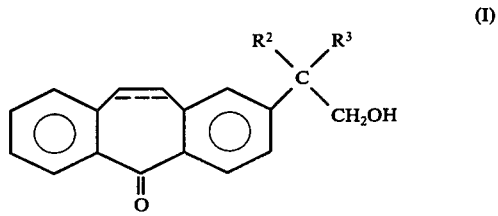

(I)

where one of R$^2$ and R$^3$ is hydrogen and the other is hydrogen, methyl, or ethyl, or together R$^2$ and R$^3$ are methylene; the dotted line refers to an optional, additional bond between the carbon atoms at the 10- and 11-positions.

2. The compound of claim 1 where both R$^2$ and R$^3$ are hydrogen.

3. The compound of claim 1 where there is a single bond between the carbon atoms at the 10- and 11-positions.

4. The compound of claim 1 where there is a double bond between the carbon atoms at the 10- and 11-positions.

5. The compound of claim 1 where said compound is 2-(5-oxo-5H-dibenzo[a,d]cyclohepten-2-yl)ethan-1-ol.

6. The compound of claim 1 where said compound is 2-(5H-dibenzo[a,d]cycloheptan-2-yl)ethan-ol.

7. The pharmaceutically acceptable esters of a hydrocarbon carboxylic acid of from 1 to 12 carbon atoms and a compound selected from the group of compounds represented by the formula:

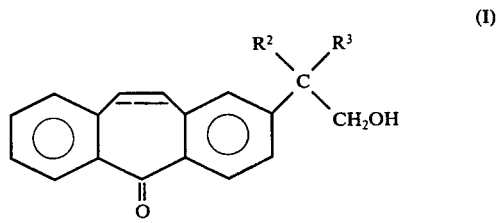

(I)

where one of $R^2$ and $R^3$ is hydrogen and the other is methyl.

8. The compound of claim 7 where there is a single bond between the carbon atoms at the 10- and 11-positions.

9. The compound of claim 7 where there is a double bond between the carbon atoms at the 10- and 11-positions.

10. The compound of claim 7 wherein said compound is 2-(5-oxo-5H-dibenzo[a,d]cyclohepten-2-yl)propan-1-ol.

11. The compound of claim 7 wherein said compound is 2-(5-oxo-5H-dibenzo[a,d]cycloheptan-2-yl)propan-1-ol.

12. The compound of claim 7 wherein said compound is d 2-(5-oxo-5H-dibenzo[a,d]cyclohepten-2-yl)propan-1-ol.

13. The compound of claim 7 wherein said compound is d 2-(5-oxo-5H-dibenzo[a,d]cycloheptan-2-yl)propan-1-ol.

14. The compound of claim 7 wherein said compound is l 2-(5-oxo-5H-dibenzo[a,d]cyclohepten-2-yl)propan-1-ol.

15. The compound of claim 7 wherein said compound is l 2-(5-oxo-5H-dibenzo[a,d]cycleheptan-2-yl)propan-1-ol.

16. A compound selected from the group consisting of 2-(5-oxo-5H-dibenzo[a,d]cyclohepten-2-yl)prop-1-yl salicylate, 2-(5-oxo-5H-dibenzo[a,d]cycloheptan-2-yl)prop-1-yl salicylate, 2-(5-oxo-5H-dibenzo[a,d]cyclohepten-2-yl)prop-1-yl 2'-acetoxybenzoate, and 2-(5-oxo-5H-dibenzo[a,d]cycloheptan-2-yl)prop-1-yl 2'-acetoxybenzoate.

17. The compound of claim 1 wherein said compound is selected from the group consisting of the acetate, propionate and butyrate esters of the compounds of Formula I.

18. The compound of claim 1 wherein said compound is 2-(5-oxo-5H-dibenzo[a,d]cyclohepten-2-yl)butan-1-ol.

19. The compound of claim 1 wherein said compound is 2-(5-oxo-5H-dibenzo[a,d]cycloheptan-2-yl)butan-1-ol.

20. The compound of claim 1 wherein said compound is 2-(5-oxo-5H-dibenzo[a,d]cyclohepten-2-yl)prop-1-en-3-ol.

21. The compound of claim 1 wherein said compound is 2-(5-oxo-5H-dibenzo[a,d]cycloheptan-2-yl)prop-1-en-3-ol.

22. 2'-(5-oxo-5H-dibenzo[a,d]cyclohepten-2-yl)prop-1'-yl 2-(5-oxo-5H-dibenzo[a,d]cyclohepten-2-yl)propionate, 2'-(5-oxo-5H-dibenzo[a,d]cycloheptan-2-yl)prop-1'-yl 2-(5-oxo-5H-dibenzo[a,d]cyclohepten-2-yl)propionate, 2'-(5-oxo-5H-dibenzo[a,d]cyclohepten-2-yl)prop-1'-yl 2-(5H-dibenzo[a,d]cyclohepten-2-yl)propionate, or 2'-(5-oxo-5H-dibenzo[a,d]cycloheptan-2-yl)prop-1'-yl 2-(5-oxo-5H-dibenzo[a,d]cycloheptan-2-yl)propionate.

23. The compound of claim 1 wherein said compound is 2-(5-oxo-5H-dibenzo[a,d]cyclohepten-2-yl)prop-1-yl acetate.

24. The compound of claim 1 wherein said compound is 2-(5-oxo-5H-dibenzo[a,d]cyclohepten-2-yl)prop-1-yl 3'-methylbutyrate.

25. The compound of claim 1 wherein said compound is 2-(5-oxo-5Hdibenzo[a,d]cyclohepten-2-yl)prop-1-yl dodecanoate.

* * * * *